(12) United States Patent
Murugesan et al.

(10) Patent No.: US 7,157,461 B2
(45) Date of Patent: Jan. 2, 2007

(54) SUBSTITUTED DIHYDROPYRIMIDINE INHIBITORS OF CALCIUM CHANNEL FUNCTION

(75) Inventors: Natesan Murugesan, Princeton Junction, NJ (US); Gergory S. Bisacchi, Newton Highlands, MA (US); William R. Ewing, Yardley, PA (US); Zhengxiang Gu, Princeton, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 151 days.

(21) Appl. No.: 10/897,040

(22) Filed: Jul. 23, 2004

(65) Prior Publication Data

US 2005/0043322 A1   Feb. 24, 2005

Related U.S. Application Data

(60) Provisional application No. 60/489,426, filed on Jul. 23, 2003.

(51) Int. Cl.
C07D 239/22 (2006.01)
A61K 31/513 (2006.01)
C07D 403/06 (2006.01)

(52) U.S. Cl. .............. 514/249; 514/269; 544/295; 544/316

(58) Field of Classification Search ......... 544/295, 544/316; 514/249, 269
See application file for complete search history.

(56) References Cited

U.S. PATENT DOCUMENTS

| | | | |
|---|---|---|---|
| 4,640,922 A | 2/1987 | Cho et al. | |
| 4,683,234 A | 7/1987 | Cho et al. | |
| 4,684,655 A | 8/1987 | Atwal | |
| 4,684,656 A | 8/1987 | Atwal | |
| 4,689,414 A | 8/1987 | Atwal | |
| 4,728,652 A | 3/1988 | Atwal | |
| 4,753,946 A | 6/1988 | Atwal et al. | |
| 4,769,371 A | 9/1988 | Atwal | |
| 4,772,602 A | 9/1988 | Cho et al. | |
| 4,824,831 A | 4/1989 | Atwal | |
| 4,855,301 A | 8/1989 | Atwal et al. | |
| 4,920,124 A | 4/1990 | Cho et al. | |
| 5,202,330 A | 4/1993 | Atwal et al. | |
| 5,403,847 A | 4/1995 | Gluchowski et al. | |
| 5,889,016 A | 3/1999 | Bruce et al. | |
| 5,942,517 A | 8/1999 | Nagarathnam et al. | |
| 6,172,066 B1 | 1/2001 | Nagarathnam et al. | |
| 6,228,861 B1 | 5/2001 | Nagarathnam et al. | |
| 6,245,773 B1 | 6/2001 | Wong et al. | |
| 6,268,369 B1 | 7/2001 | Nagarathnam et al. | |
| 6,274,585 B1 | 8/2001 | Cui et al. | |
| 2002/0010186 A1 | 1/2002 | Wong et al. | |
| 2005/0043339 A1 | 2/2005 | Murugesan et al. | |

FOREIGN PATENT DOCUMENTS

| | | |
|---|---|---|
| DE | 3840380 | 6/1989 |
| EP | 0 204 317 | 12/1986 |
| EP | 0 157 219 | 1/1988 |
| EP | 0 254 119 | 1/1988 |
| EP | 0 162 208 | 11/1989 |
| EP | 0 236 902 | 12/1990 |
| EP | 0 237 347 | 6/1991 |
| EP | 0 280 227 | 1/1992 |
| EP | 0 195 374 | 7/1992 |
| EP | 0 545 845 | 2/1996 |
| JP | 60-214778 | 10/1985 |
| JP | 60-246376 | 12/1985 |
| JP | 60-255778 | 12/1985 |
| JP | 61-130276 | 6/1986 |
| JP | 62-5968 | 2/1987 |
| JP | 62-87574 | 4/1987 |
| JP | 63-208580 | 8/1988 |
| JP | 1-249756 | 10/1989 |
| JP | 11-35483 | 2/1999 |
| WO | WO 96/14846 | 5/1996 |
| WO | WO 97/17969 | 5/1997 |
| WO | WO 97/42956 | 11/1997 |
| WO | WO 98/33791 | 8/1998 |
| WO | WO 98/51311 | 11/1998 |
| WO | WO 99/23072 | 5/1999 |
| WO | WO 00/02455 | 1/2000 |
| WO | WO 00/15845 | 3/2000 |

(Continued)

OTHER PUBLICATIONS

West, Solid Solutions, Solid state chemistry and it's applications, Wiley, New York, pp. 358 and 365, 1988.*

(Continued)

*Primary Examiner*—Deepak Rao
(74) *Attorney, Agent, or Firm*—Laurelee A. Duncan

(57) ABSTRACT

The present invention relates to substituted dihydropyrimidine inhibitors of calcium channel function having formula I

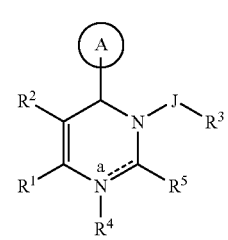

where A, a, J, $R^1$, $R^2$ $R^3$, $R^4$, and $R^5$, are defined herein; pharmaceutical compositions comprising said compounds; and methods of treating calcium channel-dependent disorders, including hypertension.

8 Claims, No Drawings

FOREIGN PATENT DOCUMENTS

| WO | WO 00/37026 | 6/2000 |
|---|---|---|
| WO | WO 00/59882 | 10/2000 |
| WO | WO 01/02561 | 1/2001 |
| WO | WO 01/19845 | 3/2001 |
| WO | WO 02/06245 | 1/2002 |
| WO | WO 02/078639 | 10/2002 |
| WO | WO 02/079149 | 10/2002 |
| WO | WO 02/079169 | 10/2002 |
| WO | WO 03/007953 | 1/2003 |

OTHER PUBLICATIONS

Vippagunta et al., Crystalline solids, Advanced Drug Delivery Reviews, 48 (2001), pp. 3-26, 2001.*

Putney, Jr. et al., Mechanisms of capaciative calcium entry, Journal of Cell Science, 114(12), pp. 2223-2229, 2001.*

Damasio, Alzheimer's Disease and Related Dementias, Cecil Textbook of Medicine, 20th Edition, vol. 2, pp. 1992-1996, 1996.*

Layzer, Degenerative Diseases of the Nervous System, Cecil Textbook of Medicine, 20th Edition, vol. 2, pp. 2050-2057, 1996.*

Simone, Oncology: Inroduction, Cecil Textbook of Medicine, 20th Edition, vol. 1, pp. 1004-1010, 1996.*

Atwal, K.S. et al., "Dihydropyrimidine Calcium Channel Blockers 5: Bicyclic Dihydropyrimidines as Potent Mimics of Dihydropyridines", Bioorganic & Medicinal Chemistry Letters, vol. 1, No. 6, pp. 291-294 (1991).

Atwal, K.S. et al., "Substituted 1,4-Dihydropyrimidines. 3. Synthesis of Selectively Functionalized 2-Hetero-1,4-dihydrpyrimidines", J. Org. Chem., vol. 54, No. 25, pp. 5898-5907 (1989).

Baylis, C. et al., "Comparison of L-Type and Mixed L- and T-Type Calcium Channel Blockers on Kidney Injury Caused by Deoxycorticosterone-Salt Hypertension in Rats", American Journal of Kidney Diseases, vol. 38, No. 6, pp. 1292-1297 (2001).

Atwal, K.S. et al., "Dihydropyrimidine Calcium Channel Blockers. 2. 3-Substituted-4-aryl-1,4-dihydro-6-methyl-5-pyrimidinecarboxylic Acid Esters as Potent Mimics of Dihydropyridines", J. Med. Chem., vol. 33, No. 9, pp. 2629-2635 (1990).

Atwal, K.S. et al., "Dihydropyrimidine Calcium Channel Blockers: 2-Heterosubstituted-4-Aryl-1,4-dihydro-6-methyl-5-pyrimidinecarboxylic Acid Esters as Potent Mimics of Dihydropyridines", J. Med. Chem., vol. 33, No. 5, pp. 1510-1515 (1990).

Atwal, K.S. et al., "Dihydropyrimidine Calcium Channel Blockers. 3. 3-Carbamoyl-4-aryl-1,2,3,4-tetrahydro-6-methyl-5-pyrimidinecarboxylic Acid Esters as Orally Effective Antihypertensive Agents", J. Med. Chem., vol. 34, No. 2, pp. 806-811 (1991).

Bhattacharjee, A. et al., "T-Type Calcium Channels Facilitate Insulin Secretion by Enhancing General Excitability in the Insulin-Secreting β-Cell Line, INS-1", Endocrinology, vol. 138, No. 9, pp. 3735-3740 (1997).

Bilici, D. et al., "Protective Effect of T-Type Calcium Channel Blocker in Histamine-Induced Paw Inflammation in Rat", Pharmacological Research, vol. 44, No. 6, pp. 527-531 (2001).

Catterall, W.A. et al., "Structure and Regulation of Voltage-Gated $Ca^{2+}$ Channels", Annu. Rev. Cell Dev. Biol., vol. 16, pp. 521-555 (2000).

Chemin, J. et al., "Specific contribution of human T-type calcium channel isotypes ($\alpha_{1G}$, $\alpha_{1H}$ and $\alpha_{1I}$) to neuronal excitability", Journal of Physiology, vol. 540, Pt. 1, pp. 3-14 (2002).

Cho, H. et al., "Dihydropyrimidines: Novel Calcium Antagonists with Potent and Long-Lasting Vasodilative and Antihypertensive Activity", J. Med. Chem., vol. 32, No. 10, pp. 2399-2406 (1989).

Cho, H. et al., "On the Tautomerism of Dihydropyrimidens: The Influence of the 2- and 5- Substituents on the Observation of Tautomers", J. Am. Chem. Soc., vol. 110, No. 14, pp. 4832-4834 (1988).

Cho, H. et al., "Regioselective Synthesis of N-Substituted Dihydropyrimidin-2(1H) or (3H)-one", Tetrahedron Letters, vol. 29, No. 42, pp. 5405-5408 (1988).

Cho, H. et al., "Synthesis of 3-Substituted 3,4-Dihydropyrimidines: N-Alkoxy-Carbonylation with Trichloromethyl Chloroformate and Alcohols", Heterocyles, vol. 27, No. 3, pp. 769-774 (1988).

Clozel, J.-P. et al., "Voltage-Gated T-Type $Ca^{2+}$ Channels and Heart Failure", Proceedings of the Association of American Physicians, vol. 111, No. 5, pp. 429-437 (1999).

Dhar, T.G.M. et al., "Design and Synthesis of Novel $\alpha_{1a}$ Adrenoceptor-Selective Antagonists. 2. Appraoches To Eliminate Opioid Agonist Metabolites via Modification of Linker and 4-Methoxycarbonyl-4-phenylpiperidine Moiety", J. Med. Chem., vol. 42, No. 23, pp. 4778-4793 (1999).

Glasser, S.P., "The Relevance of T-Type Calcium Antagonists: A Profile of Mibefradil", J. Clin. Pharmacol., vol. 38, pp. 659-669 (1998).

Harada, K. et al., "Clinical Efficacy of Efonidipine Hydrochloride, a T-type Calcium Channel Inhibitor, on Sympathetic Activites—Examination Using Spectral Analysis of Heart Rate/Blood Pressure Variabilities and $^{123}$I-Metaiodobenzylguanidine Myocardial Scintigraphy", Circulation Journal, vol. 67, pp. 139-145 (2003).

Hayashi, K. et al., "Effect of Efonidipine and ACE Inhibitors on Proteinuria in Human Hypertension With Renal Impairment", American Journal of Hypertension, vol. 16, No. 2, pp. 116-122 (2003).

Honda, M. et al., "Divergent renal vasodilator action of L- and T-type calcium antagonists in vivo", Journal of Hypertension, vol. 19, No. 11, pp. 2031-2037 (2001).

Karam, H. et al., "Contrasting Effects of Selective T- and L-Type Calcium Channel Blockade on Glomerular Damage in DOCA Hypertensive Rats", Hypertension, vol. 34, pp. 673-678 (1999).

Kochegarov, A.A., "Therapeutical application of voltage-gated calcium channel modulators", Expert Opin. Ther. Patents, vol. 12, No. 2, pp. 243-287 (2002).

Lagu, B. et al., "Design and Synthesis of Novel $\alpha_{1a}$ Adrenoceptor-Selective Antagonists. 3. Approaches To Eliminate Opioid Agonist Metabolites by Using Substituted Phenylpiperazine Side Chains", J. Med. Chem. vol. 42, No. 23, pp. 4794-4803 (1999).

Mannhold, R., "Medicinal Chemistry of DHP-Like Calcium Antagonists", Drugs of Today, vol. 30, No. 2, pp. 103-122 (1994).

Mason, R.P. et al., "Antioxidant and Cytoprotective Activities of the Calcium Channel Blocker Mibefradil", Biochemical Pharmacology, vol. 55, pp. 1843-1852 (1998).

Min, J.-Y. et al., "Mibefradil Improves β-Adrebergic Responsiveness and Intracellular $Ca^{2+}$ Handling in Hypertrophied Rat Myocardium", Exp. Biol. Med., vol. 227, No. 5, pp. 336-344 (2002).

Mulder, P. et al., "Increased Survival After Long-Term Treatment With Mibefradil, a Selective T-Channel Calcium Antagonist, in Heart Failure", J. Am. Coll. Cardiol., vol. 29, No. 2, pp. 416-421 (1997).

Nagarathnam, D. et al., "Design and Synthesis of Novel $\alpha_{1a}$ Adrenoceptor-Selective Antagonists. 1. Structure-Activity Relationship in Dihydropyrimidinones", J. Med. Chem., vol. 42, No. 23, pp. 4764-4777 (1999).

Perez-Reyes, E., "Molecular Physiology of Low-Voltage-Activated T-type Calcium Channels", Physiol. Rev., vol. 83, pp. 117-161 (2003).

Qui, C. et al., "Mibefradil prevents L-NAME-exacerbated nephrosclerosis in spontaneously hypertensive rats", Journal of Hypertension, vol. 17, No. 10, pp. 1489-1495 (1999).

Ramires, F.J.A. et al., "Myocardial Fibrosis Associated with Aldosterone or Angiotensin II Administration: Attenuation by Calcium Channel Blockade", J. Mol. Cell. Cardiol., vol. 30, pp. 475-483 (1998).

Rovnyak, G.C. et al., "Calcium Entry Blockers and Activators: Conformational and Structural Determinants of Dihydropyrimidine Calcium Channel Modulators", J. Med. Chem., vol. 38, No. 1, pp. 119-129 (1995).

Rovnyak, G.C. et al., "Dihydropyrimidine Calcium Channel Blockers. 4. Basic 3-Substituted-4-aryl-1,4-dihydropyrimidine-5-carboxylic Acid Esters. Potent Antihypertensive Agents", J. Med. Chem. vol. 35, No. 17, pp. 3254-3263 (1992).

Sandmann, S. et al., "L- and T-type calcium channel blackade—the efficacy of the calcium channel antagonist mibefradil", J. Clin. Basic. Cardiol., vol. 2, pp. 187-201 (1999).

Tanaka, H. et al., "Efonidipine Hydrochloride: A Dual Blocker of L- and T-Type $Ca^{2+}$ Channels", Cardiovascular Drug Reviews, vol. 20, No. 1, pp. 81-92 (2002).

Villame, J. et al., "Effects of Mibefradil, a T- and L-Type Calcium Channel Blocker, on Cardiac Remodeling in the UM-X7.1 Cardiomyopathic Hamster", Cardiovascular Drugs and Therapy, vol. 15, pp. 41-48 (2001).

Wong, W.C. "Design and Synthesis of Novel $\alpha_{1a}$ Adrenoceptor-Selective Antagonists. 4. Structure-Activity Relationship in the Dihydropyrimidine Series", J. Med. Chem., vol. 42, No. 23, pp. 4804-4813 (1999).

* cited by examiner

SUBSTITUTED DIHYDROPYRIMIDINE INHIBITORS OF CALCIUM CHANNEL FUNCTION

This application claims the benefit of priority to U.S. Provisional Application Ser. No. 60/489,426 filed Jul. 23, 2003, the entirety of which is incorporated herein by reference.

FIELD OF THE INVENTION

The present invention relates to dihydropyrimidine inhibitors of calcium channel function, pharmaceutical compositions comprising said compounds, and methods of treating calcium channel-dependent disorders, including hypertension.

BACKGROUND OF THE INVENTION

Calcium channels convert electrical signals in the cell membrane into an increase in intracellular calcium, thereby activating many crucial physiological processes, including muscle contraction, hormone secretion, neurotransmission, synaptic plasticity, regulation of enzymatic activites and gene expression. Calcium channels can be classified into a number of types and subtypes, for example L- (or $Ca_v1$), P/Q- (or $Ca_v2.1$), N- (or $Ca_v2.2$), R- ($Ca_v2.3$) and T- (or $Ca_v3$) types. T-type calcium channels can, for example, be subclassified into α1G (or $Ca_v3.1$), α1H (or $Ca_v3.2$), and α1I (or Cav 3.3) T channels. See, e.g., Catterall et al., *Annu. Rev. Cell Dev. Biol.* 16, 521–55, (2000); and Perez-Reyes et al., *Physiol. Rev.* 83, 117–161, (2003).

Physiologically, calcium channels are distributed widely. For example, T-type channels can be found in neurons, the heart, kidney, smooth muscle, skeletal muscle, sperm, and endocrine tissues (such as adrenal and pituitary glands and the pancreas). Consequently, T-type calcium channels are thought to be involved in autonomic nervous functions, and in regulation of cardiovascular activities such as heart rate, arterial and venous smooth muscle innervation and tone, pulmonary rate, and other critical processes.

Due to their role in modulating many physiological processes, abnormal or unwanted calcium channel activity is also associated with many disease states. Agents which antagonize or agonize the activity of calcium channels have been shown to be useful as therapies for treating a wide variety of diseases and disorders. See, e.g., WO 99/23072; EP 0545845; and Kochegarov et al., *Expert Opin. Ther. Patents*, 12, 243–287, (2002).

L-channel blockers have a well established role in the treatment of diseases such as hypertension and angina (see e.g. Mannhold et al., *Drugs of Today*, 30, 103–122, 1994). Compounds that have exclusively or predominantly T-channel blocking activity or that have dual L- and T-channel blocking activities are considered to be useful for the treatment of hypertension, angina, arrhythmia, congestive heart failure, renal disease, epilepsy, neuropathic pain, and other diseases and conditions. See, e.g., Perez-Reyes et al., *Physiol. Rev.* 83, 117–161 (2003) and WO 03/07953.

T-channel blockers are also useful for the treatment of sleep disorders, mood disorders, depression, migrane headache, neuronal excitability disorders, hyperaldosteronemia, preterm labor, urinary incontinence, brain aging, or neurodegenerative related diseases such as Alzheimer's disease. See, e.g., WO 01/02561; WO 00/02455; JP11035483 and Chernin et al., *J. Physiol.*, 540, 3–14, (2002). Additionally, T-type calcium channels play a role in pancreatic beta-cell insulin secretion. Therefore, T-type blockers may be useful for treatment of hypo- and hyperinsulinemia and the treatment and/or prevention of type 1 and type 2 diabetes as well as microvascular or macrovascular diseases associated with diabetes. See, e.g., Bhattacharjee et al., *Endocrinology*, 138, 3735–40, (1997) and WO 00/15845. T-type calcium channel blockers may also be useful in the treatment of cancer. See, e.g., WO 00/59882 and WO 01/019845.

Drugs such as mibefradil and efonidipine which block both T and L calcium channels have been shown to be useful or potentially useful in a variety of disease states. Such drugs may have therapeutic advantages over calcium channel blockers that predominantly target the L-channel. For example, mibefradil was shown to be useful for the treatment of hypertension and angina and did not show the negative side-effects including inotropy, reflex tachycardia, vasoconstrictive hormone release or peripherial edema, which are often shown by predominantly L-channel blockers. See, e.g., Sandman et al., *J. Clin. Basic Cardiol.*, 2, 187–201 (1999) and Glasser et al., *J. Clin. Pharmacol.*, 38, 659–669 (1998). Also, mibefradil has been shown to be potentially cardioprotective (see e.g. Villame, *Cardiovascular Drugs and Therapy*, 15, 41–48 (2001) and Ramires, et al., *J. Mol. Cell Cardiol.*, 30, 475–483, (1998)) and renal protective (see e.g. Honda, J. et al., Hypertension, 19, 2031–2037 (2001); Baylis et al., *Am. J. Kidney Dis.*, 38, 1292–1297 (2001); Qiu, et al., *J. Hvpertension*, 1489–1495 (1999); and Karam et al., *Hypertension*, 34, 673–678, (1999)). Also, unlike most predominant L-channel blockers, mibefradil has been shown to be potentially useful in the treatment of heart failure. See, e.g., Clozel, et al., *Proceedings of the Association of American Physicians*, 111, 429–437 (1999); Mulder, et al., *Journal of the American College of Cardiology*, 29, 416 (1997); and Meissner, et al., *Exp. Biol. Med* 227, 336–44, (2002). Mibefradil may also be useful in the treatment of atherosclerosis (see e.g. Mason, et al., *Biochemical Pharmacology*, 55, 1843–1852, (1998)) and inflammation (see, e.g., Bilici, et al., *Pharmacological Research*, 527–531 (2001)). Efonidipine, another calcium channel blocker with a combination of T- and L-channel blocking activities, also shows therapeutic advantages over pure L-channel blockers. See, e.g., Harada, et al., *Circ. J.* 67, 139–145 (2003); Hayashi, et al., *Amer. Heart J.*, 16, 116–122 (2003); and Tanaka, et al., *Cardiovascular Drug Reviews*, 20, 81–92 (2002).

SUMMARY OF THE INVENTION

The present invention provides substituted pyrimidine inhibitors of calcium channel function, pharmaceutical compositions containing such substituted pyrimidine compounds, and methods for treating calcium channel dependent disorders using such compounds and compositions. Specifically, the invention provides compounds of Formula I:

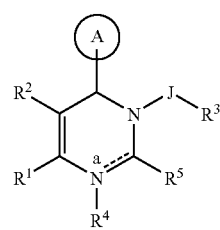

enantiomers, diastereomers, solvates and salts thereof
wherein
A is aryl or heteroaryl, each of which may be optionally substituted with $Z^{1a}$, $Z^{2a}$ and one or more $Z^{3a}$
a is a single or a double bond where $R^4$ is absent;
J is alkylene, alkenylene, or alkynylene any of which may be optionally substituted with $Z^{1b}$, $Z^{2b}$ and one or more $Z^{3b}$;
$R^1$ is hydrogen, alkyl, alkenyl or alkynyl any of which may be optionally substituted with $Z^{1c}$, $Z^{2c}$ and one or more $Z^{3c}$;
$R^2$ is
  (a) alkyl, alkoxy or aryloxy, each group optionally substituted with $Z^{1d}$, $Z^{2d}$ and one or more $Z^{3d}$;
  (b) cyano or nitro; or
  (c) —C(O)$R^5$ or C(O)O$R^5$;
$R^3$ is
  (a) cycloalkyl, aryl, heterocyclo or heteroaryl, any of which may be optionally substituted with $Z^{1e}$, $Z^{2e}$ and one or more $Z^{3e}$; or
  (b) —N$R^6$ $R^7$, —N($R^6$)C(O) $R^7$, —N($R^6$)C(O)O$R^7$, —N($R^6$)C(O)—N$R^7R^8$, —OC(O)N$R^6R^7$, —N$R^6$S(O)$_t$ $R^7$, —S(O)$_t$N$R^6R^7$ or S(O)$_tR^6$ where t is 1 or 2;
$R^4$ is
  (a) absent;
  (b) hydrogen; or
  (c) alkyl, cycloalkyl, aryl, heterocyclo, heteroaryl, (aryl)alkyl, (cycloalkyl)alkyl, (heterocyclo)alkyl or (heteroaryl)alkyl any of which may be optionally substituted with $Z^{1f}$, $Z^{2f}$ and one or more $Z^{3f}$;
$R^5$ is
  (a) hydrogen; or
  (b) alkyl, cycloalkyl, aryl, heterocyclo, heteroaryl, (aryl)alkyl, (cycloalkyl)alkyl, (heterocyclo)alkyl or (heteroaryl)alkyl any of which may be optionally substituted with $Z^{1g}$, $Z^{2g}$ and one or more $Z^{3g}$;
$R^{5a}$ is
  (a) hydrogen; or
  (b) amino, alkyl, cycloalkyl, aryl, heterocyclo, heteroaryl, (aryl)alkyl, (cycloalkyl)alkyl, (heterocyclo)alkyl or (heteroaryl)alkyl any of which may be optionally substituted with $Z^{1h}$, $Z^{2h}$ and one or more $Z^{3h}$;
$R^6$, $R^7$ and $R^8$ are independently
  (a) hydrogen;
  (b) alkyl, alkenyl, alkynyl, cycloalkyl, aryl, heterocyclo, or heteroaryl, any group of which may be optionally substituted with $Z^{1i}$, $Z^{2i}$ and one or more $z^{3i}$; or
  (c) $R^6$ and $R^7$ are optionally taken together to form
    (i) an alkylene or alkenylene group;
    (ii) —N=C$R^9$—;
    (iii) —N=N—; or
$R^9$ is
  (a) hydrogen; or
  (b) alkyl, cycloalkyl, aryl, heterocyclo, heteroaryl, (aryl)alkyl, (cycloalkyl)alkyl, (heterocyclo)alkyl or (heteroaryl)alkyl any of which may be optionally substituted with $Z^{1j}$, $Z^{2i}$j and one or more $z^{3j}$;
$Z^{1a-1j}$, $Z^{2a-2j}$, and $Z^{3a-3j}$ are optional substituents independently selected from
  (1) $R^{10}$, where $R^{10}$ is
    (i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl;
    (ii) a group (i) which is itself substituted by one or more of the same or different groups (i); or
  (iii) a group (i) or (ii) which is independently substituted by one or more (preferably 1 to 3) of the following groups (2) to (13) of the definition of $Z^{1a-j}$,
  (2) —OH or —O$R^{10}$,
  (3) —SH or —S$R^{10}$,
  (4) —C(O)$_t$H, —C(O)$_tR^{10}$, or —O—C(O)$R^{10}$, where t is 1 or 2,
  (5) —SO$_3$H, —S(O)$_tR^{10}$, or S(O)$_t$N($R^{11}$) $R^{10}$,
  (6) halo,
  (7) cyano,
  (8) nitro,
  (9) —U$^1$—N $R^{12}R^{13}$,
  (10) —U$^1$—N($R^{11}$)—U$^2$—N $R^{12}R^{13}$,
  (11) —U$^1$—N($R^{14}$)—U$^2$—$R^{10}$,
  (12) —U$^1$—N($R^{14}$)—U$^2$—H,
  (13) oxo;
$U^1$ and $U^2$ are each independently
  (1) a single bond,
  (2) —U$^3$—S(O)$_t$—U$^4$—,
  (3) —U$^3$—C(O)—U$^4$—,
  (4) —U$^3$—C(S)—U$^4$—,
  (5) —U$^3$—O—U$^4$—,
  (6) —U$^3$—S—U$^4$—,
  (7) —U$^3$—O—C(O)—U$^4$—,
  (8) —U$^3$—C(O)—O—U$^4$—,
  (9) —U$^3$—C(=N$R^{15}$)—U$^4$—, or
  (10) —U$^3$—C(O)—C(O)—U$^4$—;
$R^{11}R^{12}$, $R^{13}$, and $R^{15}$
  (1) are each independently hydrogen or a group provided in the definition of $Z^{1a-j}$; or
  (2) $R^{12}$ and $R^{13}$ may together be alkylene or alkenylene, completing a 3- to 8-membered saturated or unsaturated ring together with the atoms to which they are attached, which ring is unsubstituted or substituted with one or more groups listed in the definition of $Z^{1a-j}$, or
  (3) $R^{12}$ or $R^{13}$, together with $R^{11}$, may be alkylene or alkenylene completing a 3- to 8-membered saturated or unsaturated ring together with the nitrogen atoms to which they are attached, which ring is unsubstituted or substituted with one or more groups listed in the definition of $Z^{1a-j}$, or
  (4) $R^{12}$ and $R^{13}$ together with the nitrogen atom to which they are attached may combine to form a group —N=C $R^{16}R^{17}$ where $R^{16}$ and $R^{17}$ are each independently H or a group provided in the definition of $R^{10}$; and
$U^3$ and $U^4$ are each independently
  (1) a single bond,
  (2) alkylene,
  (3) alkenylene,
  (4) alkynylene.

This invention is also directed to pharmaceutical compositions comprising at least one compound of formula I, and a pharmaceutically acceptable vehicle, carrier or diluent.

This invention is also directed to methods of treating a mammalian host to relieve one or more calcium channel-dependent disorders comprising administering to said host in need of such treatment an effective amount a pharmaceutical composition comprising a compound of formula (I).

DETAILED DESCRIPTION OF THE INVENTION

The following are definitions of terms used in this specification. The initial definition provided for a group or term herein applies to that group or term throughout the present specification, individually or as part of another group, unless otherwise indicated.

The term "alkyl" as used herein by itself or as part of another group refers to straight and branched chain hydrocarbons, containing 1 to 20 carbons, preferably 1 to 10 carbons, more preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like. Lower alkyl groups, that is, alkyl groups of 1 to 6 carbon atoms, are often most preferred.

The term "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like.

The term "alkynyl" as used herein by itself or as part of another group refers to straight or branched chain hydrocarbon groups having 2 to 12 carbon atoms, preferably 2 to 4 carbon atoms, and at least one triple carbon to carbon bond, such as ethynyl, 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like.

Where alkyl groups as defined above have single bonds for attachment to two other groups, they are termed "alkylene" groups. Similarly, where alkenyl groups as defined above and alkynyl groups as defined above, respectively, have single bonds for attachment to two other groups, they are termed "alkenylene groups" and "alkynylene groups" respectively. Examples of alkylene, alkenylene and alkynylene groups include:

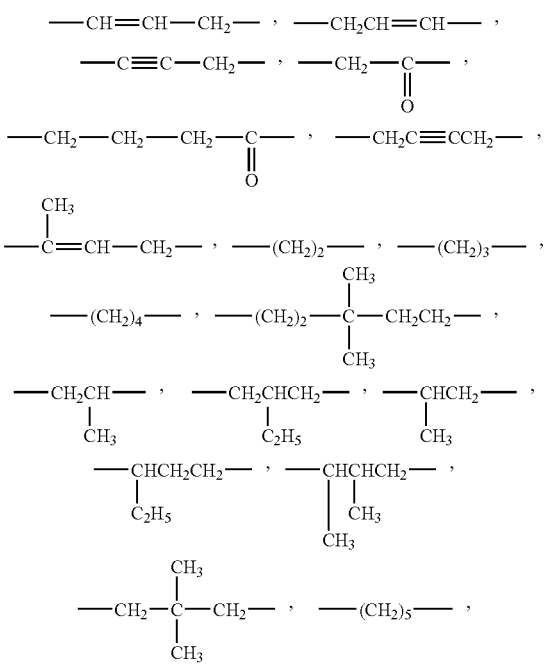

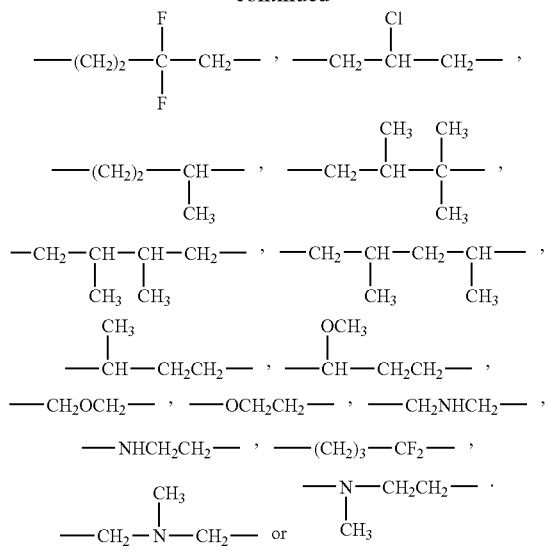

The term "cycloalkyl" as used herein by itself or as part of another group refers to saturated and partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 7 carbons, forming the ring. The rings of multi-ring cycloalkyls may be either fused, bridged and/or joined through one or more spiro union to 1 or 2 aromatic, cycloalkyl or heterocyclo rings. Exemplary cycloalkyl groups include cyclopropyl, cyclobutyl, cyclopentyl, cyclohexyl, cycloheptyl, cyclooctyl, cyclodecyl, cyclododecyl, cyclopentenyl, cyclohexenyl, cycloheptenyl, cyclooctenyl, cyclohexadienyl, cycloheptadienyl,

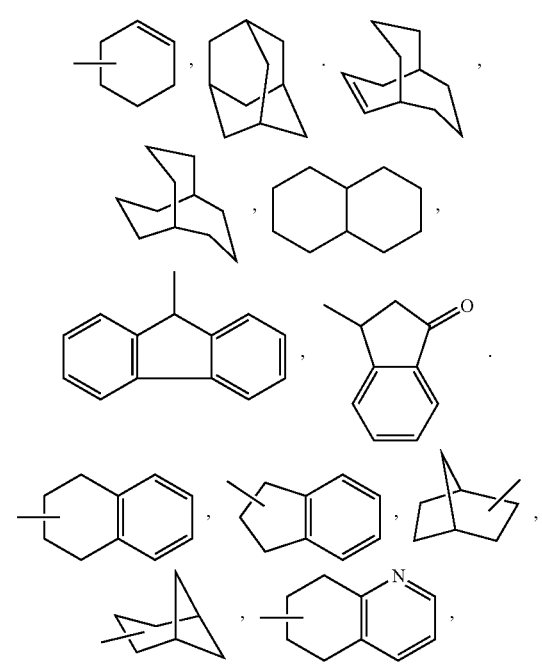

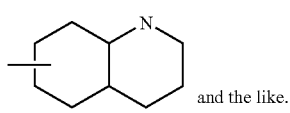 and the like.

The term "cycloalkylene" as employed herein refers to a "cycloalkyl" group which includes free bonds and thus is a linking group such as

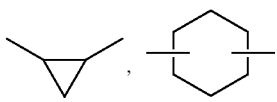

and the like.

The terms "ar" or "aryl" as used herein by itself or as part of another group refer to aromatic homocyclic (i.e., hydrocarbon) monocyclic, bicyclic or tricyclic aromatic groups containing 6 to 14 carbons in the ring portion (such as phenyl, biphenyl, naphthyl (including 1-naphthyl and 2-naphthyl) and antracenyl) and may optionally include one to three additional rings (either cycloalkyl, heterocyclo or heteroaryl) fused thereto. Examples include:

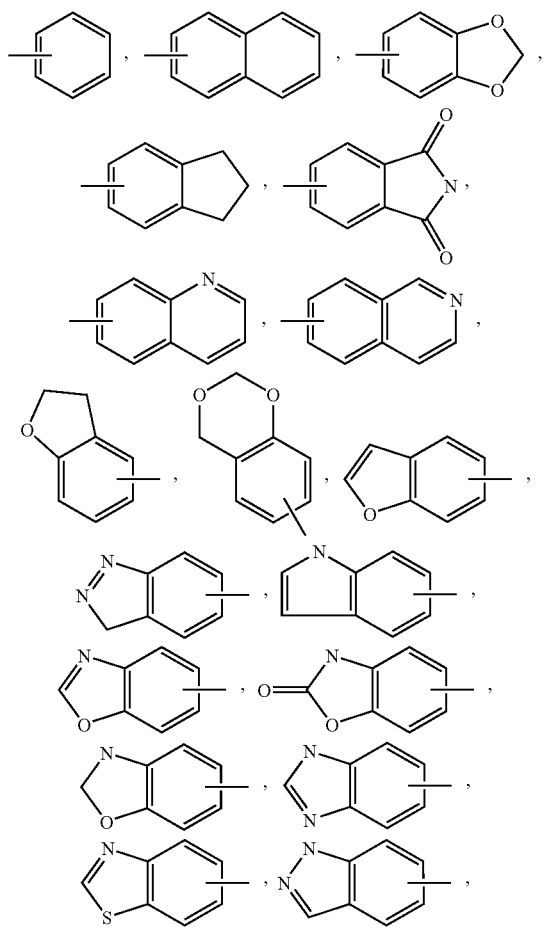

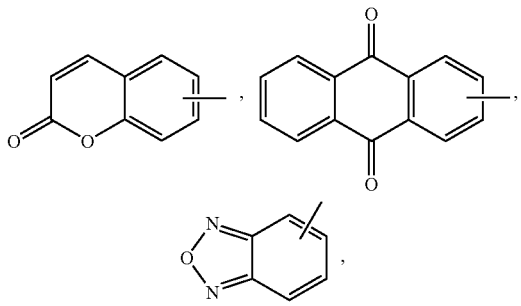

and the like.

The terms "halogen" and "halo" as used herein by itself or as part of another group refer to fluorine, chlorine, bromine and iodine. Haloalkyl refers to an alkyl chain substituted with from one to three halogens.

The term "heteroaryl" as used herein by itself or as part of another group refers to monocyclic and bicyclic aromatic rings containing from 5 to 10 atoms, which includes 1 to 4 hetero atoms such as nitrogen, oxygen or sulfur, and such rings fused to an aryl, cycloalkyl, heteroaryl or heterocyclo ring, where the nitrogen and sulfur heteroatoms may optionally be oxidized and the nitrogen heteroatoms may optionally be quatemized. Examples of heteroaryl groups include the following:

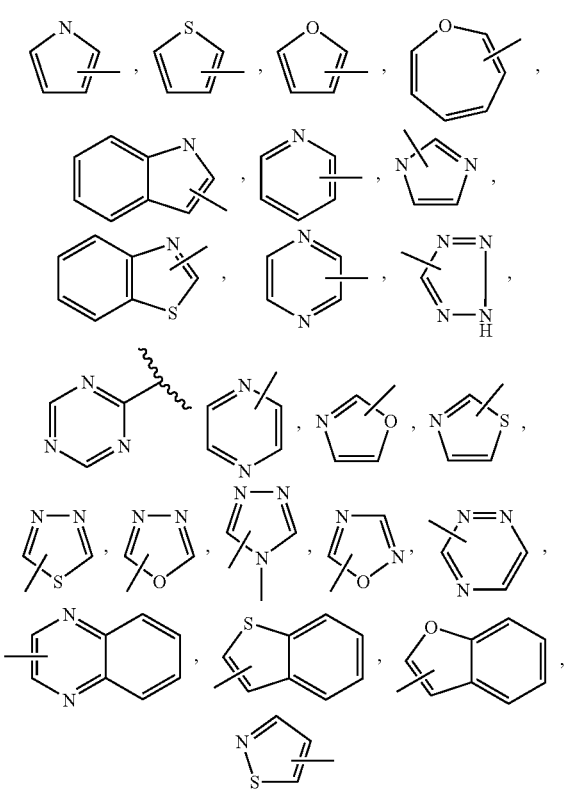

and the like.

The terms "heterocyclic" or "heterocyclo" as used herein by itself or as part of another group refer to optionally substituted, fully saturated or partially unsaturated cyclic groups (for example, 3 to 13 member monocyclic, 7 to 17 member bicyclic, or 10 to 20 member tricyclic ring systems, preferably containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valance allows. The rings of multi-ring heterocycles may be either fused, bridged and/or joined through one or more spiro unions. Exemplary heterocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl,

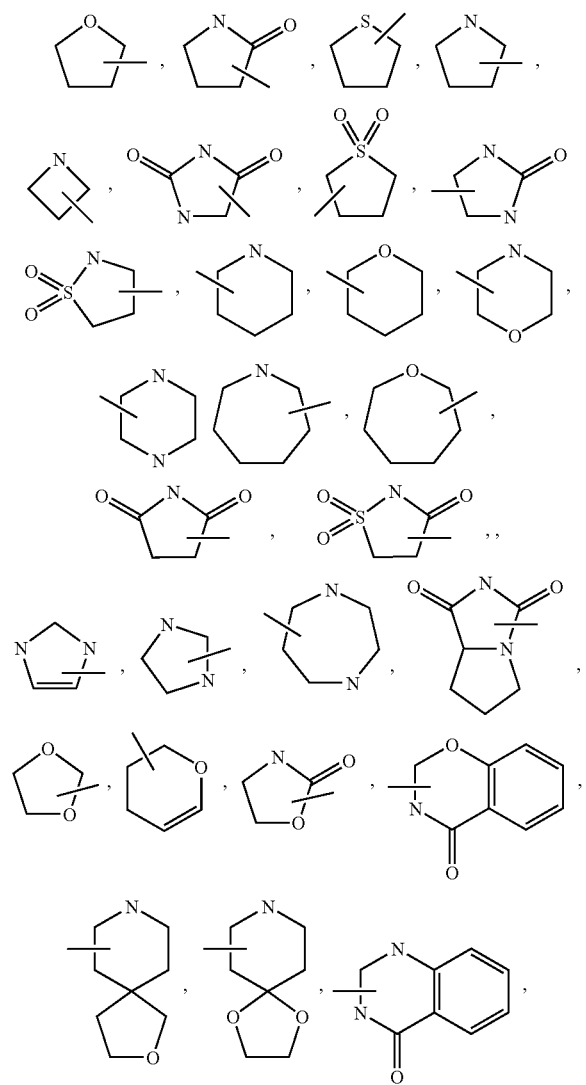

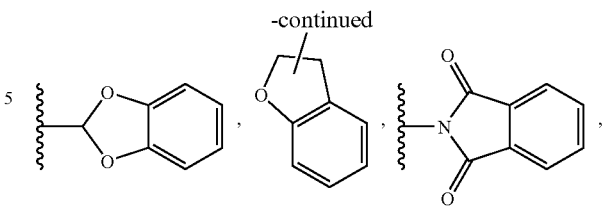

and the like.

The term "ring" encompasses homocyclic (i.e., as used herein, all the ring atoms are carbon) or "heterocyclic" (i.e., as used herein, the ring atoms include carbon and one to four heteroatoms selected from N, O and /or S, also referred to as heterocyclo), where, as used herein, each of which (homocyclic or heterocyclic) may be saturated or partially or completely unsaturated (such as heteroaryl).

A subscript "x" associated with carbon atom (i.e. "$C_x$") indicates the total number of possible carbon atoms in the group. For example the terms "$C_{1-6}$alkyl" indicates a lower alkyl having from 1 to six carbon atoms. Likewise, the term "$C_{1-6}$haloalkyl" designates a haloalkyl group having from 1 to 6 carbon atoms, and "$C_{1-6}$alkoxy" indicates an alkoxy group containing from 1 to 6 carbon atoms.

Throughout the specification, groups and substituents thereof may be chosen to provide stable moieties and compounds.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of formula I which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug", as employed herein, denotes a compound which, upon administration to a subject, undergoes chemical conversion by metabolic or chemical processes to yield a compound of the formula I, or a salt and/or solvate thereof. Solvates of the compounds of formula I are preferably hydrates. Any tautomers which may exist are also contemplated herein as part of the present invention. Various forms of prodrugs are well known in the art. For examples of such prodrug derivatives, see:

a) *Design of Prodrugs*, edited by H. Bundgaard, (Elsevier, 1985) and *Methods in Enzymology*, Vol.42, p. 309–396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, pp. 113–191 (1991); and c) H. Bundgaard, *Advanced Drug Delivery Reviews*, 8, 1–38 (1992), each of which is incorporated herein by reference.

All stereoisomers of the present compounds, such as those which may exist due to asymmetric carbons on the R substituents, including enantiomeric forms (which may exist even in the absence of asymmetric carbons, e.g., atropisomers) and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

Methods of Preparation

The compounds of the present invention may be prepared by methods such as those illustrated in the following Schemes 1–6. Solvents, temperatures, pressures, and other reaction conditions may be selected by one of ordinary skill in the art. Starting materials are commercially available or readily prepared by one of ordinary skill in the art.

The preparation of pyrimidine core intermediates 4 are illustrated in Scheme 1 as follows. See J. Med. Chem. 32, 2399 (1989). Briefly, an aryl (depicted)or heteroaryl aldehyde 1 is condensed with ketone 2 in the presence of a base such as pyridine to afford a benzylidine intermediate 3, which is reacted with an amidine compound to afford the pyrimidine core structure 4.

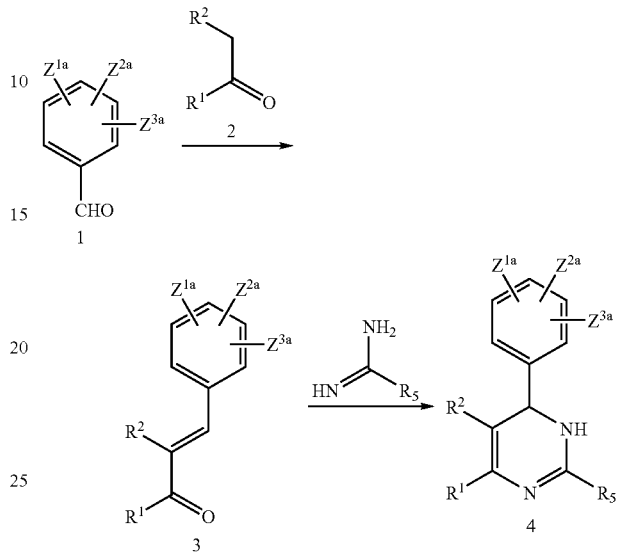

Scheme 1

As described in Scheme 2, pyrimidine core intermediate 4 is alkylated in the presence of a base, such as sodium hydide with a side-chain intermediate 5, to provide intermediate 6. As described herein, L is a leaving group such as bromo, iodo, or tosyl, and P is an amino protecting group such as Boc or Cbz. An acid such as TFA or HCl is used to remove acid-labile protecting groups P to provide intermediate 7. Condensation of the side-chain amine of 7 with an acid chloride in the presence of base (e.g. a triethylamine) or an acid in the presence of DCC affords the compound of the invention 1a.

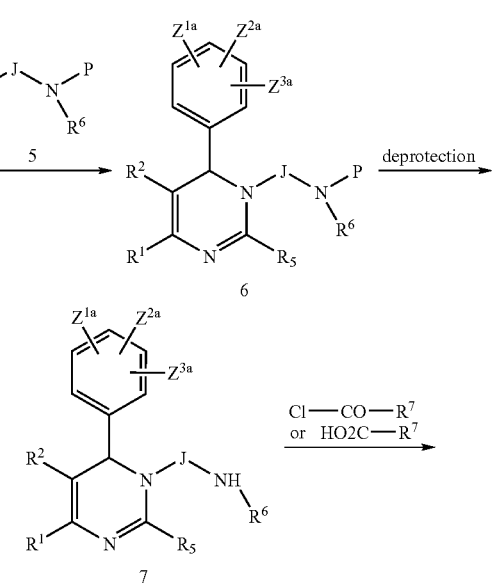

Scheme 2

-continued

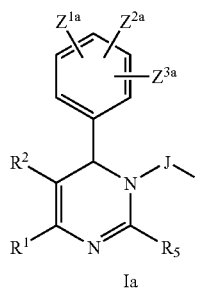

Ia

As illustrated in Scheme 3, treatment of intermediate 7 with a a) sulfonyl chloride, b) chloroformate, c) N,N-dialkylcarbamoylchloride, or d) isocyanate provides compounds of the invention Ib, Ic, Id, Ie, respectively.

Scheme 3

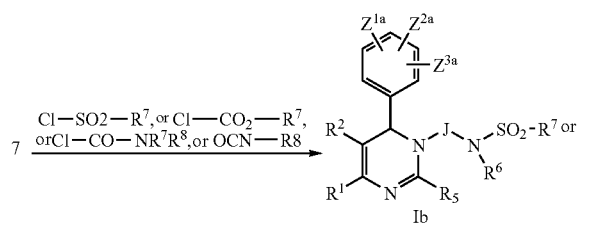

Ib

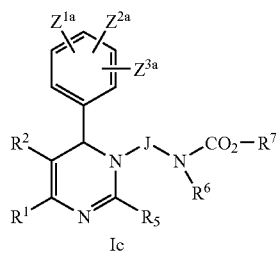

Ic

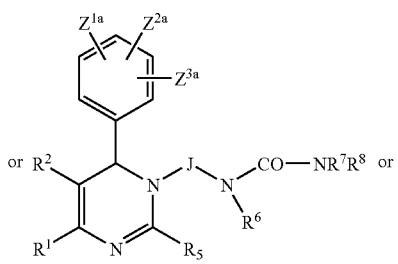

Id

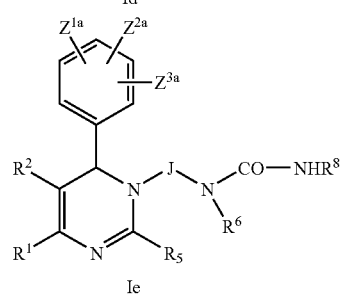

Ie

As described in Scheme 4, alkylation of pyrimidine core intermediate 4 with protected acid 8 provides intermediate 9, which following deprotection, affording 10, and condensation of the acid group with an amine in the presence of DCC provides compound of the invention If.

Scheme 4

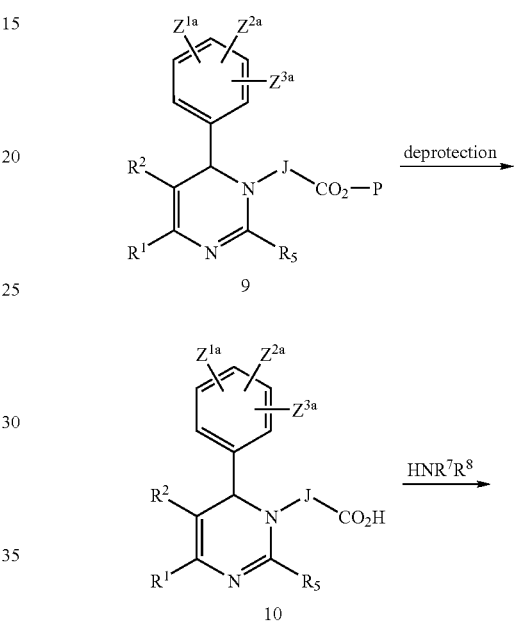

If

Scheme 5 illustrates that the treatment of core intermediate 4 with a compound 11 having two leaving groups L and L' in the presence of a base such as sodium hydride provides intermediate 12 which upon reaction with a urea in the presence of a base (e.g. sodium hydride) provides compound of the invention 1 g.

Alternatively, treatement of core intermediate 4 with a compound 11 having a leaving group and a protected alcohol provides intermediate 14, which upon deprotection provides intermediate 15. Reaction of 15 with an alkane or arene sulfonyl chloride (such as methane sulfonyl chloride or toluene sulfonyl chloride) in the presence of a base such as triethylamine provides intermediate 16 which can be reacted with a urea 19 to provide product of the invention Ig.

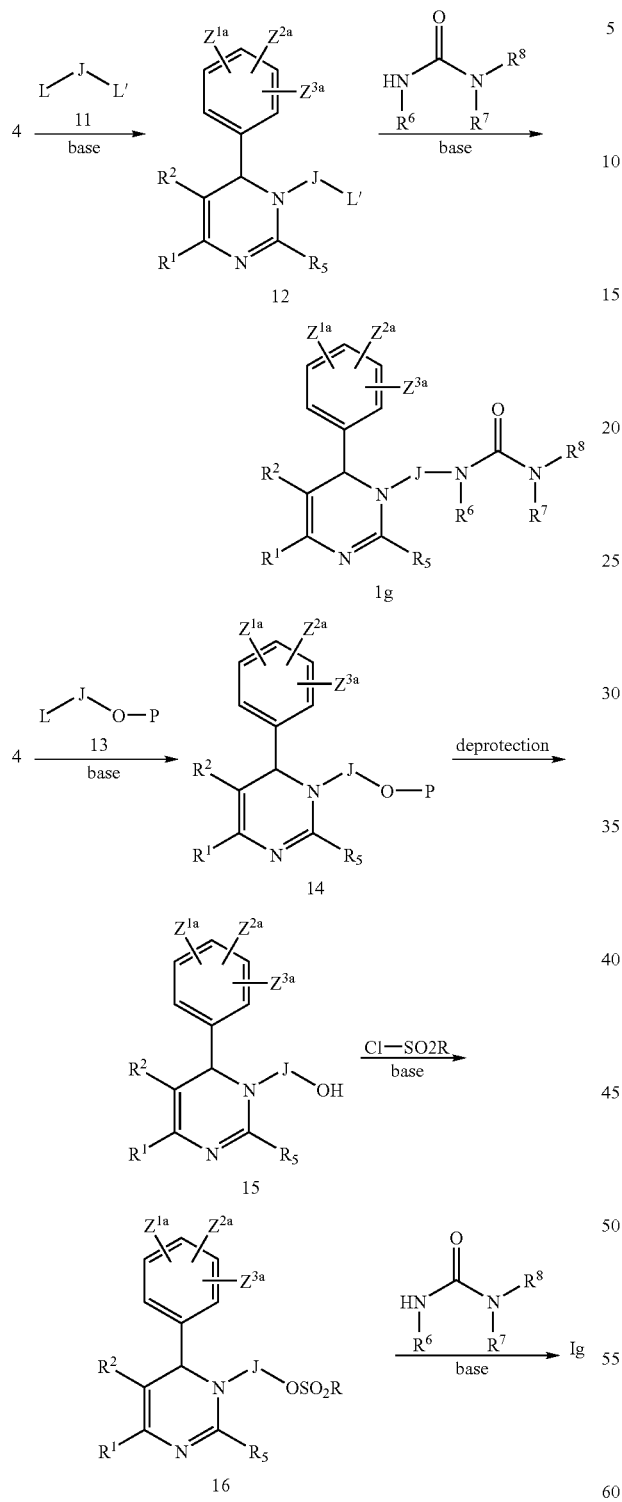

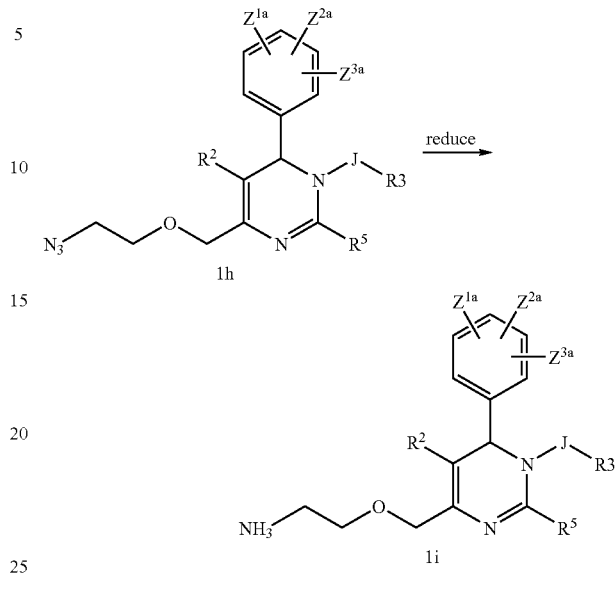

Finally, as shown in Scheme 6, a compound of the invention Ih may contain functionality in the R1 group, for example an azide, which can be further modified. Reduction of the azide group of Ih with hydrogen in the presence of a palladium catalyst provides product of the invention Ig.

PREFERRED COMPOUNDS

Preferred compounds within the scope of formula I, enantiomers, diastereomers, solvates and salts thereof, are those in which:

J is alkylene optionally substituted with $Z^{1b}$, $Z^{2b}$ and one or more $Z^{3b}$ (especially where J is n-propyl); and/or $R^1$ is alkyl optionally substituted with $Z^{1c}$, $Z^{2c}$ and one or more $Z^{3c}$; (especially where $R^1$ is $C_{1-6}$alkyl) and/or $R^2$ is $C(O)R^{5a}$ or $C(O)OR^{5a}$ (especially $C(O)OR^{5a}$); and/or $R^4$ is absent; and/or $R^5$ is
  (a) hydrogen; or
  (b) alkyl, aryl or alkoxy, each group of which is optionally substituted with $z^{1g}$, $Z^{2g}$ and one or more $Z^{3g}$;
  (especially where $R^5$ is
    (a) hydrogen, $C_{1-6}$alkyl, $C_{1-6}$haloalkyl, $C_{1-6}$alkoxy; or
    (b) phenyl optionally substituted by one or more groups selected from halo, cyano, nitro, $C_{1-6}$alkyl, $C_{1-6}$haloalkyl and/or $C_{1-6}$alkoxy); and/or $R^3$ is —$N(R^6)C(O)O$ $R^7$, —$N(R^6)C(O)$ $R^7$, or —$N(R^6)C(O)$—$NR^7R^8$; and/or A is aryl, optionally substituted with $Z^{1a}$, $Z^{2a}$ and one or more $Z^{3a}$ (especially where A has the formula

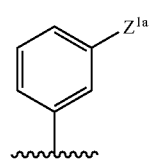

and wherein $Z^{1a}$ is selected from $Z^{1a}$ is halo, nitro, cyano, $C_{1-6}$alkyl, $C_{1-6}$haloalkyl or $C_{1-6}$alkoxy).

More preferred compounds within the scope of formula I are those having formula II

II enantiomers, diastereomers, solvates and salts thereof, wherein:

$Z^{1a}$ is halo, nitro, cyano, $C_{1-6}$alkyl, $C_{1-6}$haloalkyl or $C_{1-6}$alkoxy (especially halo or nitro);

J is alkylene (especially n-propyl);

$R^1$ is $C_{1-6}$alkyl;

$R^3$ is —N($R^6$)C(O)O $R^7$, —N($R^6$)C(O) $R^7$ or —N($R^6$)C(O)—NR$^7$R$^8$;

$R^{5a}$ is $C_{1-6}$alkyl (especially methyl, ethyl or isopropyl); and $R^5$ is (a) hydrogen, $C_{1-6}$alkyl, $C_{1-6}$haloalkyl, $C_{1-6}$alkoxy; or (b) phenyl optionally substituted by one or more groups selected from halo, cyano, nitro, $C_{1-6}$alkyl, $C_{1-6}$haloalkyl and/or $C_{1-6}$alkoxy (especially where $R^5$ is methyl, ethyl, isopropyl, $CF_3$ or phenyl).

Especially preferred are those compounds within the scope of formula II, enantiomers, diastereomers, solvates and salts thereof, wherein:

J is n-propyl;

$R^3$ is —N($R^6$)C(O)—NR$^7$R$^8$; and $R^6$ and $R^7$ are taken together to form an alkylene group.

Even more especially preferred compounds within the scope of formula II, enantiomers, diastereomers, solvates and salts thereof, have formula III

III

Other especially preferred compounds within the scope of formula II, enantiomers, diastereomers, solvates and salts thereof, are those in which:

J is n-propyl;

$R^3$ is —N($R^6$)C(O) $R^7$;

$R^6$ is hydrogen or alkyl; and $R^7$ is selected from wherein $Z^{1h-2h}$ are selected from halogen, nitro, cyano, $C_{1-6}$alkyl, $C_{1-6}$haloalkyl and/or $C_{1-6}$alkoxy (especially methyl, t-butyl, $CF_3$, fluoro, and chloro). Particularly preferred $R^7$ groups are those in which $R^7$ is selected from:

Other especially preferred compounds within the scope of formula II, enantiomers, diastereomers, solvates and salts thereof, are those in which:

J is n-propyl;

$R^3$ is N($R^6$)C(O)O$R^7$; and $R^6$ and $R^7$ are independently selected from hydrogen and $C_{1-6}$alkyl.

Especially preferred compounds within the scope of formula I are selected from:

(i)

6-(3-Chlorophenyl)-1,6-dihydro-2,4-dimethyl-1-[3-[methyl(4-phenoxybenzoyl)amino]propyl]-5-pyrimidinecarboxylic acid, 1-methylethyl ester;

6-(3-Chlorophenyl)-1,6-dihydro-2,4-dimethyl-1-[3-[methyl(phenylacetyl)amino]propyl]-5-pyrimidinecarboxylic acid, 1-methylethyl ester;

6-(3-Chlorophenyl)-1,6-dihydro-2,4-dimethyl-1-[3-[methyl[(2E)-1-oxo-3-phenyl-2-propenyl]amino]propyl]-5-pyrimidinecarboxylic acid, 1-methylethyl ester;

6-(3-Chlorophenyl)-1,6-dihydro-2,4-dimethyl-1-[3-[methyl(4-phenoxybenzoyl)amino]propyl]-5-pyrimidinecarboxylic acid, 1-methylethyl ester, enantiomer A;

6-(3-Chlorophenyl)-1,6-dihydro-2,4-dimethyl-1-[3-[methyl(4-phenoxybenzoyl)amino]propyl]-5-pyrimidinecarboxylic acid, 1-methylethyl ester, enantiomer B;

1-[3-[[4-(4-Chlorophenoxy)benzoyl]methylamino]propyl]-6-(3-chlorophenyl)-1,6-dihydro-2,4-dimethyl-5-pyrimidinecarboxylic acid, 1-methylethyl ester;

6-(3-Chlorophenyl)-1,6-dihydro-4-methyl-2-(1-methylethyl)-1-[3-[methyl(4-phenoxybenzoyl)amino]propyl]-5-pyrimidinecarboxylic acid, 1-methylethyl ester;

6-(3-Chlorophenyl)-1,6-dihydro-4-methyl-1-[3-[methyl(phenylacetyl)amino]propyl]-2-phenyl-5-pyrimidinecarboxylic acid, 1-methylethyl ester;

6-(3-Chlorophenyl)-1,6-dihydro-2,4-dimethyl-1-[3-[methyl[(2E)-1-oxo-3-phenyl-2-propenyl]amino]propyl]-5-pyrimidinecarboxylic acid, 1-methylethyl ester;

6-(3-Chlorophenyl)-1-[3-[[4-(2,4-difluorophenoxy)benzoyl]methylamino]propyl]-1,6-dihydro-2,4-dimethyl-5-pyrimidinecarboxylic acid, 1-methylethyl ester;

6-(3-Chlorophenyl)-1-[3-[[4-(1,1-dimethylethyl)benzoyl]methylamino]propyl]-1,6-dihydro-2,4-dimethyl-5-pyrimidinecarboxylic acid, 1-methylethyl ester, enantiomer A;

6-(3-Chlorophenyl)-1-[3-[[4-(1,1-dimethylethyl)benzoyl]methylamino]propyl]-1,6-dihydro-2,4-dimethyl-5-pyrimidinecarboxylic acid, 1-methylethyl ester, enantiomer A;

6-(3-Chlorophenyl)-1-[3-[[4-(1,1-dimethylethyl)benzoyl]methylamino]propyl]-1,6-dihydro-2,4-dimethyl-5-pyrimidinecarboxylic acid, 1-methylethyl ester, enantiomer B;

6-(3-Chlorophenyl)-1-[3-[[4-(1,1-dimethylethyl)benzoyl]methylamino]propyl]-1,6-dihydro-4-methyl-2-(trifluoromethyl)-5-pyrimidinecarboxylic acid, 1-methylethyl ester;

6-(3-Chlorophenyl)-1,6-dihydro-4-methyl-1-[3-[methyl(4-phenoxybenzoyl)amino]propyl]-2-(trifluoromethyl)-5-pyrimidinecarboxylic acid, 1-methylethyl ester; or (ii) enantiomers, diastereomers, solvates and salts of (i) thereof.

Even more especially preferred compounds within this scope are selected from:

(i)

6-(3-Chlorophenyl)-1,6-dihydro-2,4-dimethyl-1-[3-[methyl(4-phenoxybenzoyl)amino]propyl]-5-pyrimidinecarboxylic acid, 1-methylethyl ester, enantiomer A;

6-(3-Chlorophenyl)-1,6-dihydro-2,4-dimethyl-1-[3-[methyl(4-phenoxybenzoyl)amino]propyl]-5-pyrimidinecarboxylic acid, 1-methylethyl ester, enantiomer B;

6-(3-Chlorophenyl)-1-[3-[[4-(1,1-dimethylethyl)benzoyl]methylamino]propyl]-1,6-dihydro-2,4-dimethyl-5-pyrimidinecarboxylic acid, 1-methylethyl ester, enantiomer A;

6-(3-Chlorophenyl)-1-[3-[[4-(1,1-dimethylethyl)benzoyl]methylamino]propyl]-1,6-dihydro-2,4-dimethyl-5-pyrimidinecarboxylic acid, 1-methylethyl ester, enantiomer B;

(ii) enantiomers, diastereomers, solvates and salts of (i) thereof.

Utility

The compounds of formula I and salts thereof are antagonists of calcium channels (especially T-type and/or L-type calcium channels) and are useful in treatment of calcium channel-dependent disorders. They are thus useful as antihypertensive agents. By the administration of a composition having one (or a combination) of the compounds of this invention, the blood pressure of a hypertensive mammalian (e.g., human) host is reduced. They are also useful in portal hypertension, hypertension secondary to treatment with erythropoietin and low renin hypertension.

The compounds of the present invention are also useful in the treatment of disorders related to renal, glomerular and mesangial cell function, including acute (such as ischemic, nephrotoxic, or glomerulonephritis) and chronic (such as diabetic, hypertensive or immune-mediated) renal failure, diabetic nephropathy, glomerular injury, renal damage secondary to old age or related to dialysis, nephrosclerosis (especially hypertensive nephrosclerosis), nephrotoxicity (including nephrotoxicity related to imaging and contrast agents and to cyclosporine), renal ischemia, primary vesicoureteral reflux, glomerulosclerosis and the like. The compounds of this invention are also useful in the treatment of disorders related to paracrine and endocrine function. The compounds of this invention are also useful in the treatment of diabetic nephropathy, hypertension-induced nephropathy, and IGA-induced nephropathy.

The compounds of the present invention are also useful in the treatment of endotoxemia or endotoxin shock as well as hemorrhagic shock. The compounds of the present invention are also useful in alleviation of pain, including neuropathic pain, peripheral pain and pain associated with cancer, such as the pain associated with prostate cancer, and bone pain associated with bone cancer. The compounds of the present invention are further useful in the prevention and/or reduction of end-organ damage associated with cell-proliferation.

The compounds of the present invention are also useful in hypoxic and ischemic disease and as anti-ischemic agents for the treatment of, for example, cardiac, renal and cerebral ischemia and reperfusion (such as that occurring following cardiopulmonary bypass surgery), coronary and cerebral vasospasm, and the like.

In addition, the compounds of this invention are also useful as anti-arrhythmic agents; anti-anginal agents; antifibrillatory agents; anti-asthmatic agents; anti-atherosclerotic and anti-arteriosclerotic agents (including anti-transplantation arteriosclerotic agents); additives to cardioplegic solutions for cardiopulmonary bypasses; adjuncts to thrombolytic therapy; and anti-diarrheal agents. The compounds of this invention may be useful in therapy for myocardial infarction; therapy for peripheral vascular disease (e.g., Raynaud's disease, intermittent claudication and Takayashu's disease); treatment of cardiac hypertrophy (e.g., hypertrophic cardiomyopathy); treatment of primary pulmonary hypertension (e.g., plexogenic, embolic) in adults and in the newborn and pulmonary hypertension secondary to heart failure, radiation and chemotherapeutic injury, or other trauma; treatment of central nervous system vascular disorders, such as stroke, migraine and subarachnoid hemorrhage; treatment of central nervous system behavioral disorders; treatment of gastrointestinal diseases such as ulcerative colitis, Crohn's disease, gastric mucosal damage, ulcer, inflammatory bowel disease and ischemic bowel disease; treatment of gall bladder or bile duct-based diseases such as cholangitis; treatment of pancreatitis; regulation of cell growth; treatment of benign prostatic hypertrophy; restenosis following angioplasty or following any procedure including transplantation and stenting; therapy for congestive heart failure including inhibition of fibrosis; inhibition of left ventricular dilatation, remodeling and dysfunction; and treatment of hepatotoxicity and sudden death. The compounds of this invention are useful in the treatment of sickle cell disease including the initiation and/or evolution of the pain crises of this disease; treatment of the deleterious consequences of tumors such as hypertension resulting from hemangiopericytoma; treatment of early and advanced liver disease and injury including attendant complications (e.g., hepatotoxicity, fibrosis and cirrhosis); treatment of spastic diseases of the urinary tract and/or bladder; treatment of hepatorenal syndrome; treatment of immunological diseases involving vasculitis such as lupus, systemic sclerosis, mixed cryoglobulinemia; and treatment of fibrosis associated with renal dysfunction and hepatotoxicity. The compounds of this invention are useful in therapy for metabolic and neurological disorders; cancer; insulin-dependent and non insulin-dependent diabetes mellitus; neuropathy; retinopathy; epilepsy; hemorrhagic and ischemic stroke; bone remodeling; psoriasis; and chronic inflammatory diseases such as arthritis, rheumatoid arthritis, osteoarthritis, sarcoidosis and eczematous dermatitis (all types of dermatitis).

The compounds of this invention are additionally useful in the treatment of disorders involving bronchoconstriction and disorders of chronic or acute pulmonary inflammation such as chronic obstructive pulmonary disease (COPD) and adult respiratory distress syndrome (ARDS).

The compounds of this invention are also useful in the treatment of sexual dysfunction in both men (erectile dysfunction, for example, due to diabetes mellitus, spinal cord injury, radical prostatectomy, psychogenic etiology or any other cause) and women by improving blood flow to the genitalia, especially, the corpus cavemosum.

The compounds of this invention are also useful in the treatment of dementia, including Alzheimer's dementia, senile dementia and vascular dementia.

Additionally the compounds of the present invention are further useful in the reduction of general morbidity and/or mortality as a result of the above utilities.

The present invention thus provides methods for the treatment of these disorders, comprising the step of administering to a subject in need thereof at least one compound of the formula I in an amount effective therefor. Other therapeutic agents such as those described below may be employed with the inventive compounds in the present methods. In the methods of the present invention, such other therapeutic agent(s) may be administered prior to, simultaneously with or following the administration of the compound(s) of the present invention.

The effective amount of a compound of the present invention may be determined by one of ordinary skill in the art, and includes exemplary dosage amounts for a human of from about 0.1 to about 100 mg/kg, preferably about 0.2 to about 50 mg/kg and more preferably from about 0.5 to about 25 mg/kg of body weight (or from about 1 to about 2500 mg, preferably from about 5 to about 500 mg) of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to calcium channel-dependent disorders.

The present invention also provides pharmaceutical compositions comprising at least one of the compounds of the formula I capable of treating a calcium channel-dependent disorder in an amount effective therefor, and a pharmaceutically acceptable vehicle, carrier or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation or called for by accepted pharmaceutical practice.

The compounds of the formula I may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally. For example, the active substance can be utilized in a composition such as tablet, capsule, solution or suspension containing about 5 to about 500 mg per unit dosage of a compound or mixture of compounds of formula I or in topical form for wound healing (0.01 to 5% by weight compound of formula I, 1 to 5 treatments per day). They may be compounded in a conventional manner with a physiologically acceptable vehicle or carrier, excipient, binder, preservative, stabilizer, flavor, etc., or with a topical carrier. The compounds of formula I can also be formulated in compositions such as sterile solutions or suspensions for parenteral administration. About 0.1 to 500 milligrams of a compound of formula I may be compounded with a physiologically acceptable vehicle, carrier, excipient, binder, preservative, stabilizer, etc., in a unit dosage form as called for by accepted pharmaceutical practice. The amount of active substance in these compositions or preparations is preferably such that a suitable dosage in the range indicated is obtained.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono-or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene). For example, the compounds of the invention may be administered topically to treat peripheral vascular diseases and as such may be formulated as a cream or ointment.

The compounds of the present invention may be employed alone or in combination with each other and/or other suitable therapeutic agents. For example, the compounds of this invention can be formulated in combination with endothelin converting enzyme (ECE) inhibitors, such as phosphoramidon; thromboxane receptor antagonists such as ifetroban; potassium channel openers; thrombin inhibitors (e.g., hirudin and the like); growth factor inhibitors such as modulators of PDGF activity; platelet activating factor (PAF) antagonists; anti-platelet agents such as GPIIb/IIIa blockers (e.g., abciximab, eptifibatide, and tirofiban), P2Y (AC) antagonists (e.g., clopidogrel, ticlopidine and CS-747), and aspirin; anticoagulants such as warfarin, low molecular weight heparins such as enoxaparin, Factor VIIa inhibitors, and Factor Xa inhibitors such as those described in U.S. Ser. No. 09/496,571 filed Feb. 2, 2000; renin inhibitors; angiotensin converting enzyme (ACE) inhibitors such as captopril, zofenopril, fosinopril, ceranapril, alacepril, enalapril, delapril, pentopril, quinapril, ramipril, lisinopril and salts of such compounds; neutral endopeptidase (NEP) inhibitors; vasopepsidase inhibitors (dual NEP-ACE inhibitors) such as omapatrilat and gemopatrilat; HMG CoA reductase inhibitors such as pravastatin, lovastatin, atorvastatin, simvastatin, NK-104 (a.k.a. itavastatin, or nisvastatin or nisbastatin) and ZD-4522 (a.k.a. rosuvastatin, or atavastatin or visastatin); squalene synthetase inhibitors; fibrates; bile acid sequestrants such as questran; niacin; anti-atherosclerotic agents such as ACAT inhibitors; MTP inhibitors such as those described in U.S. Ser. No. 09/007,938 filed Jan. 16, 1998; calcium channel blockers such as amlodipine besylate; potassium channel activators; alpha-adrenergic agents, beta-adrenergic agents such as carvedilol and metoprolol; anti-arrhythmic agents, such as dofetilide, quinidine, ibutilide, propofanone, amiodarone; diuretics, such as chlorothiazide, hydrochlorothiazide, flumethiazide, hydroflumethiazide, bendroflumethiazide, methylchlorothiazide, trichloromethiazide, polythiazide or benzothiazide as well as ethacrynic acid, tricrynafen, chlorthalidone, furosemide, musolimine, bumetanide, triamterene, amiloride and spironolactone and salts of such compounds; thrombolytic agents such as tissue plasminogen activator (tPA), recombinant tPA, streptokinase, urokinase, prourokinase and anisoylated plasminogen streptokinase activator complex (APSAC); anti-diabetic agents such as biguanides (e.g. metformin), glucosidase inhibitors (e.g., acarbose), insulins, meglitinides (e.g., repaglinide), sulfonylureas (e.g., glimepiride, glyburide, and glipizide), biguanide/glyburide combinations such as those described in U.S. Ser. No. 09/432,465 filed Nov. 3, 1999 and U.S. Ser. No. 09/460,920 filed Dec. 14, 1999); thiozolidinediones (e.g. troglitazone, rosiglitazone and pioglitazone), and PPAR-gamma agonists; mineralocorticoid receptor antagonists such as spironolactone and eplerenone; growth hormone secretagogues such as those described in U.S. Ser. No. 09/417,180 filed Oct. 12, 1999 and U.S. Ser. No. 09/506,749 filed Feb. 18, 2000; aP2 inhibitors such as those described in U.S. Ser. No. 09/391,053 filed Sep. 7, 1999 and U.S. Ser. No. 09/390,275 filed Sep. 7, 1999 digitalis; ouabian; non-steroidal antiinflammatory drugs (NSAIDS) such as aspirin and ibuprofen; phosphodiesterase inhibitors such as PDE III inhibitors (e.g., cilostazol) and PDE V inhibitors (e.g., sildenafil); protein tyrosine kinase inhibitors; antiinflammatories; antiproliferatives such as methotrexate, FK506 (tacrolimus, Prograf), mycophenolate and mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); antimetabolites such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as paclitaxel (Taxol®), docetaxel (Taxotere®), and epothilones A–F or their analogs or derivatives; plant-derived products, such as vinca alkaloids, epipodophyllotoxins, taxanes; and topoisomerase inhibitors; prenyl-protein transferase inhibitors; and miscellaneous agents such as, hydroxyurea, procarbazine, mitotane, hexamethylmelamine, platinum coordination complexes such as cisplatin and carboplatin); cyclosporins; steroids such as prednisone or dexamethasone; gold compounds; cytotoxic drugs such as azathiprine and cyclophosphamide; TNF-alpha inhibitors such as tenidap; anti-TNF antibodies or soluble TNF receptor such as etanercept (Enbrel) rapamycin (sirolimus or Rapamune), leflunimide (Arava); and cyclooxygenase-2 (COX-2) inhibitors such as celecoxib (Celebrex) and rofecoxib (Vioxx).

The compounds of this invention may also be formulated with, or useful in conjunction with, antifungal and immunosuppressive agents such as amphotericin B, cyclosporins and the like to counteract the glomerular contraction and nephrotoxicity secondary to such compounds. The compounds of this invention may also be used in conjunction with hemodialysis.

If formulated as a fixed dose, such combination products employ the compounds of this invention within the dosage range described below and the other pharmaceutically active agent within its approved dosage range. The above other therapeutic agents, when employed in combination with the compounds of the present invention, may be used, for example, in those amounts indicated in the Physicians' Desk Reference (PDR) or as otherwise determined by one of ordinary skill in the art.

The following assays may be employed in ascertaining the degree of activity of a compound as an antagonists of calcium channels (especially T-type and/or L-type calcium channels). Compounds described in the following Examples are exceptional calcium channel antagonists having $IC_{50}$ at concentrations of <20 μM.

Aortic Ring Protocol:

Male Sprague-Dawley rats (250–300 g) were euthanized by $CO_2$ and cervical dislocation. The thoracic aorta was removed and placed in physiological salt solution (PSS) of the following composition, in mM: 118.4 NaCl, 4.7 KCl, 1.2 $MgCl_2$, 1.2 $KH_2PO_4$, 1.9 $CaCl_2$, 25.0 $NaHCO_3$, and 10.1 glucose. The aorta was cleaned of adherent connective tissue and cut into rings approximately 3 mm wide. The endothelium was removed from each ring by placing the ring on a dissecting probe and gently rolling on PSS-moistened filter paper. Each rat aortic ring was mounted for isometric force recording on stainless steel wires in a 10 ml organ chamber between a micrometer for control of tissue length and a GRASS® FT-03 force transducer. Mechanical responses were recorded using a PowerLab® data acquisition system. The organ chambers contained PSS aerated with 95% $O_2$, 5% $CO_2$ to maintain the pH at 7.4. The experiments were performed at 37° C. The tissues were gradually stretched over a 2 hr equilibration period to approximately 2 g preload. Compounds were tested for the ability to produce relaxation of aortic rings that were contracted with 80 mM KCl.

Patch-clamp Electrophysiology:

T-and L-type calcium currents were studied using cell lines stably expressing the cloned human T-(alpha1H) and L-type calcium ion channel genes. Membrane current recordings were made with Axopatch 200A and 200B integrating patch-clamp amplifiers (Axon Instruments, Foster City, Calif.) using the whole-cell variant of the patch-clamp technique. The bath solution, which replaced the cell culture media during experiments, for T-type calcium current experiments contained (in mM): 140 NaCl, 5 $CaCl_2$, 4 KCl, 1 $MgCl_2$, 10 Glucose, 10 HEPES (pH 7.35, NaOH). The patch pipette filling solution used T-type calcium current experiments experiments contained (in mM): 130 KCl, 1 $CaCl_2$, 1 $MgCl_2$, 5 ATP-$K_2$, 10 EGTA, 10 HEPES (pH 7.2, KOH). The bath solution for L-type calcium current experiments contained (in mM): 103 NaCl, 30 $BaCl_2$, 4 CsCl, 1 $MgCl_2$, 10 glucose, 10 HEPES (pH 7.35, NaOH). The pipette solution used in L-type calcium current experiments contained (in mM): 20 CsCl, 20 tetraethylammonium chloride, 82 glutamate, 3 ATP-Mg, 0.5 $NaH_2PO_4$, 3 $Na_2$-creatine $PO_4$, 11 EGTA, 10 HEPES (pH 7.25, CsOH). The bath and pipette solutions used in L-type calcium current studies minimized current "rundown" over time. Barium has a greater conductance than calcium through the L-type calcium channel and was used as charge carrier in L-type calcium channel experiments to increase whole-cell current amplitude. No protein was present in bath solutions, so concentrations of test agents represent free or unbound test agent.

T-type calcium currents were elicited by repetitive 200 ms voltage steps to −30 mV applied from a holding potential of −80 mV. The repetitive voltage steps were continuously applied at a frequency of 0.2 Hz throughout experiments. Effects of compounds were calculated by measuring inhibition of peak current elicited during voltage steps. Peak current was measured from the holding current at −80 mV and used to calculate per cent inhibition. L-type calcium currents were elicited by repetitive 200 ms voltage steps to 30 mV applied from a holding potential of −50 mV. The repetitive voltage steps were continuously applied at a frequency of 0.2 Hz throughout experiments. Effects of compounds were calculated by measuring inhibition of peak current recorded at 30 mV. Data were sampled at rates at least two times the low pass filter rate. The flow rate was kept constant throughout the experiments (~5 ml/min). All membrane currents were recorded at 25° C.

The following Examples illustrate embodiments of the present invention, and are not intended to limit the scope of the claims. Abbreviations employed herein are defined below.

ABBREVIATIONS

BOC=tert-butoxycarbonyl
CBZ=carbobenzyloxy
$CH_3CN$=acetonitrile
DCC=dicyclohexylcarbodiimide
DCE=dichloroethane
DCM=dichloromethane
DMAP=4-dimethylaminopyridine
DIPEA or DIEA=N,N-diisopropylethylamine
DME=1,2-dimethoxyethane
DMF=dimethyl formamide
EDCI=1-3-dimethylaminopropyl)-3-ethylcarbodiimide
$Et_2O$=diethyl ether
HOBT=1-hydroxybenzotriazole
EtOAc=ethyl acetate
HCl=hydrochloric acid KOH=potassium hydroxide
K₂CO₃=potassium carbonate
LiAlH₄=lithium aluminum hydride
MeCN=acetonitrile
MeOH=methanol
MgSO₄=magnesium sulfate
NaH=sodium hydride
NaOH=sodium hydroxide
NMP=1-methyl-2-pyrrolidinone
SOCl₂=thionyl chloride
TEA=triethylamine
THF=tetrahydrofurane
bp=boiling point
g=gram(s)
mg=milligram(s)
ml=milliliter
μl=microliter
l=liter
mmol=millimole
μmol=micromole
mol=mole
mp=melting point
RT=room temperature NMR (Nuclear Magnetic resonnance was performed on a Brucker 200 spectrometer (s=singulet, d=doublet, t=triplet, dd=doublet of doublet, m=multiplet) Elementary analysis were carried on a Carlo-Erba Mod 106 elementary analyzer Compounds of the Examples are identified by the example and step in which they are prepared (for example, "1A" denotes the title compound of step A of Example 1), or by the example only where the compound is the title compound of the example (for example, "4" denotes the title compound of Example 4).

EXAMPLE 1

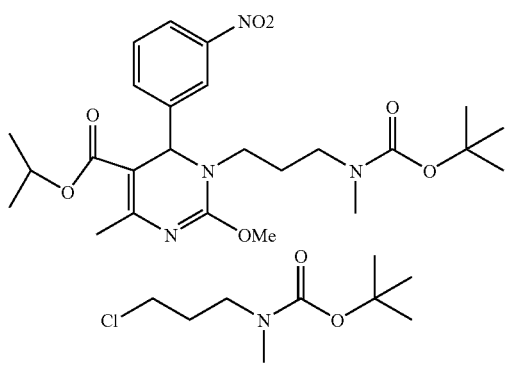

1A

To N-methyl-3-chloropropylamine hydrochloride (2.88 g, 20 mmol) and Di-tert-butyl dicarbonate (4.3 g, 20 mmol) in THF (100 ml) was added triethylamine (5.6 ml, 40 mmol) dropwise. The mixture was stirred at RT overnight. The solution was diluted with 4:1 EtOAc:hexane, washed with water, brine, dried and concentrated to give 1A (4.28 g, 100%)

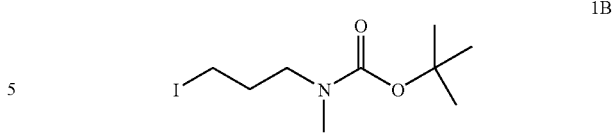

1B

To a stirred solution of 1A (1.45 g, 7 mmol) in acetone (70 ml) was added sodium iodide (10.5 g, 70 mmol). The mixture was stirred at 50° C. for 20 h. The solution was cooled and diluted with CH₂Cl₂, filtered and concentrated. Purification by flash chromatography on silica gel (1:9 EtOAc/hexane as the elutant) gave 1B as an oil (800 mg, 38%).

1C: Title Compound

To a stirred solution of 2-Methoxy-6-methyl-4-(3-nitrophenyl)-1,4-dihydro-pyrimidine-5-carboxylic acid isopropyl ester (synthesized by the method in the reference J of Med. Chem, 1990, 33(5), 1510) (3.6 g, 11 mmol) in DMF (10 ml) at 0° C. sodium hydride (480 mg, 12 mmol) was added in portions. To this mixture was added 1B (3.6 g, 12 mmol) in DMF (1 ml) and the solution was stirred at RT for 5 h. The solution was diluted with EtOAc, washed with water, brine, dried and concentrated. Purification by flash chromatography on silica gel (1:4 EtOAc/hexane as the elutant) gave 1C as an oil (3.6 g, 66%).

EXAMPLE 2

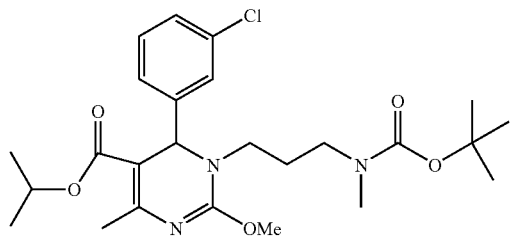

Example 2 was prepared using the method described in Example 1 utilizing the appropriate starting materials.

Separation of Enantiomers of Example 2

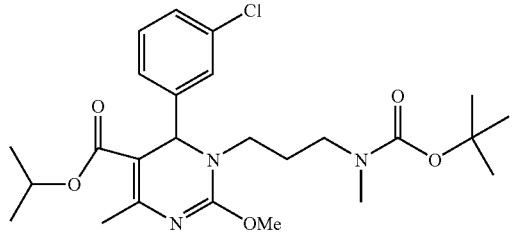

Enantiomers A and B

The compound of Example 2 was subjected to chiral separation using chiral prep HPLC (Chiralpak AD 5 cm×50 cm 2 μm) & 5% IPA/hexane as eluant). The enantiomer eluting first from the prep column was designated Enantiomer A and the second compound that eluted was designated Enantiomer B.

EXAMPLE 3 (BMS-585548)

6-(3-Chloro-phenyl)-2,4-dimethyl-1-{3-[methyl-(4-phenoxy-benzoyl)-amino]-propyl}-1,6-dihydro-pyrimidine-5-carboxylic acid isopropyl ester

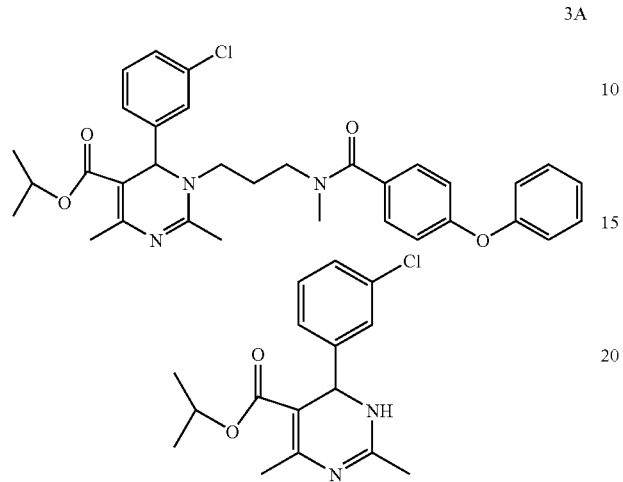

3A was synthesized by known methods using the appropriate starting materials. *J. Med. Chem,* 33(5), 1510 (1990)

3B

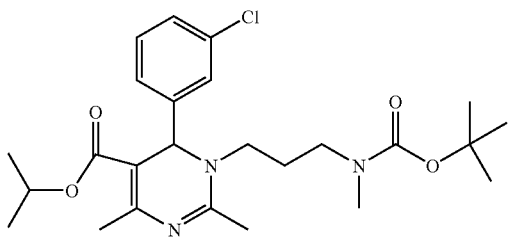

3B was prepared using the method described in 1C substituting 3A (195 mg, 0.64 mmol) for 1B (228 mg, 0.76 mmol). 3B was obtained as a light yellow oil

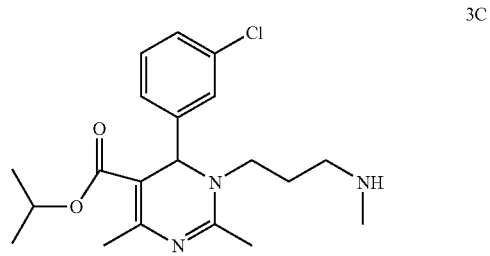

3C was prepared using the method described in Example 1 substituting 1C with 3B (260 mg, 0.54 mmol). 3C was obtained as a oil.

Title Compound

To a solution of 3C (12.8 mg, 0.055 mmole) in 1 ml of methylene chloride, p-phenoxybenzoylchloride (25 mg, 0.066 mmole) and triethylamine (15.3 uL, 0.11 mmole) were added and stirred at room temperature for three hours. The mixture was concentrated and purified by preparative liquid chromatography to provide the title compound (20.3 mg) as a gum. MS (M+H) 574.

The following compounds in Table 1 have been synthesized utilizing the procedures described in Example 3, utilizing the appropriate starting materials.

TABLE 1

| Compound number | $R^7$ | $R^5$ | HPLC Purity (%) | Mass M+ H |
|---|---|---|---|---|
| 4 | ![benzyl] | Me | 97 | 496 |

TABLE 1-continued
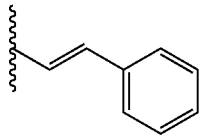
| Compound number | R⁷ | R⁵ | HPLC Purity (%) | Mass M+ H |
|---|---|---|---|---|
| 5 | 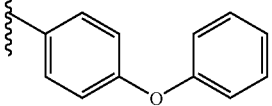 | Me | 97 | 508 |
| 6 | 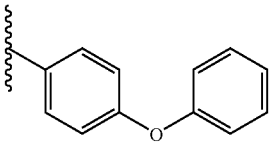 Enantiomer A | Me | 100 | 574 |
| 7 | 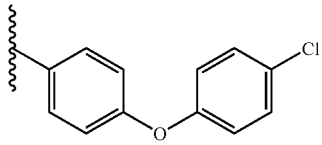 Enantiomer B | Me | 100 | 574 |
| 8 | 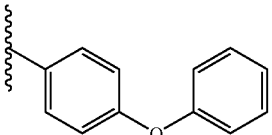 | Me | 97 | 608 |
| 9 | 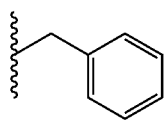 | isopropyl | 97 | 602 |
| 10 | 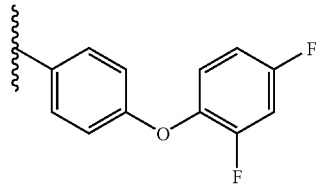 | Phenyl | 99 | 558 |
| 11 |  | Me | >97 | 610 |

TABLE 1-continued

| Compound number | R⁷ | R⁵ | HPLC Purity (%) | Mass M+ H |
|---|---|---|---|---|
| 12 | 4-tert-butylphenyl | Me | 97 | 538 |
| 13 | 4-tert-butylphenyl (Enantiomer A) | Me | 100 | 538 |
| 14 | 4-tert-butylphenyl (Enantiomer B) | Me | 100 | 538 |
| 15 | 4-tert-butylphenyl | CF₃ | 98 | 592 |
| 16 | 4-phenoxyphenyl | CF₃ | 98 | 628 |

EXAMPLE 17

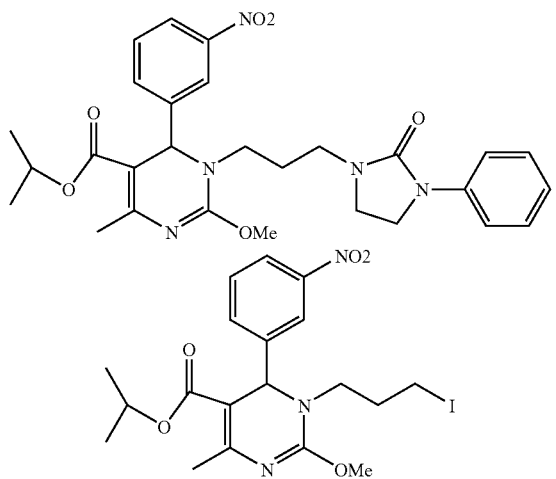

To 1D (3.7 g, 11.12 mmol) in DMF (15 ml) was added sodium hydride (60% dispersion in mineral oil, 320 mg, 13.3 mmol). The mixture was stirred at RT for 15 min followed by addition of 1,3-diiodopropane (5.1 ml, 44.5 mmol). The solution was stirred at RT for 2.7 h and was diluted with EtOAc, washed with water, brine, dried and concentrated. Purification by flash chromatography on silica gel (1:5 EtOAc/hexane as the elutant) gave 17A as a oil (1.1 g, 85%).

Title Compound

To 1-Phenyl-imidazolidin-2-one (39 mg, 0.24 mmol) in DMF (0.5 ml) was added sodium hydride (60% dispersion in mineral oil, 6 mg, 0.25 mmol) followed by 17A (100 mg, 0.2 mmol). The solution was quenched with water, extracted with EtOAc, washed with water, brine, dried and concentrated. Purification by flash chromatography on silica gel (2:3 EtOAc/hexane as the elutant) gave the title compound as a oil (61 mg, 60%).

What is claimed is:

1. A compound having the formula II

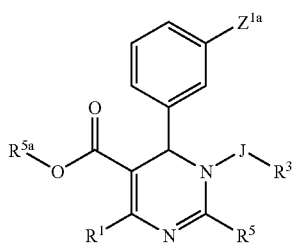

or an enantiomer, diastereomer, or salt, thereof wherein:
$Z^{1a}$ is halo, nitro, cyano, $C_{1-6}$alkyl, $C_{1-6}$haloalkyl, or $C_{1-6}$alkoxy;
J is n-propylene;
$R^1$ is $C_{1-6}$alkyl;
$R^3$ is —N($R^6$)C(O)—N$R^7R^8$;
$R^{5a}$ is $C_{1-6}$alkyl;
$R^5$ is
(a) hydrogen, $C_{1-6}$alkyl, $C_{1-6}$haloalkyl, or $C_{1-6}$alkoxy; or
(b) phenyl optionally substituted by one or more groups selected from halo, cyano, nitro, $C_{1-6}$alkyl, $C_{1-6}$haloalkyl, and/or $C_{1-6}$alkoxy;
$R^6$ and $R^7$ are taken together to form a —$CH_2CH_2$- group; and
$R^6$ is $C_{1-6}$alkyl.

2. A compound having the formula II

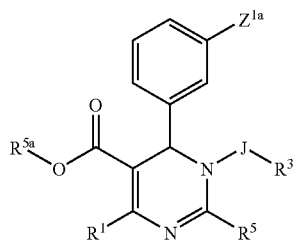

or an enantiomer, diastereomer, or salt, thereof, wherein:
$Z^{1a}$ is halo, cyano, $C_{1-6}$alkyl, $C_{1-6}$haloalkyl, $C_{1-6}$alkoxy;
J is n-propylene;
$R^1$ is $C_{1-6}$alkyl;
$R^3$ is —N($R^6$)C(O)$R^7$;
$R^{5a}$ is $C_{1-6}$alkyl;
$R^5$ is
(a) hydrogen, $C_{1-6}$alkyl, $C_{1-6}$haloalkyl, or $C_{1-6}$alkoxy; or
(b) phenyl optionally substituted by one or more groups selected from halo, cyano, nitro, $C_{1-6}$alkyl, $C_{1-6}$haloalkyl, and/or $C_{1-6}$alkoxy;
$R^6$ is hydrogen or $C_{1-6}$alkyl; and
$R^7$ is selected from,

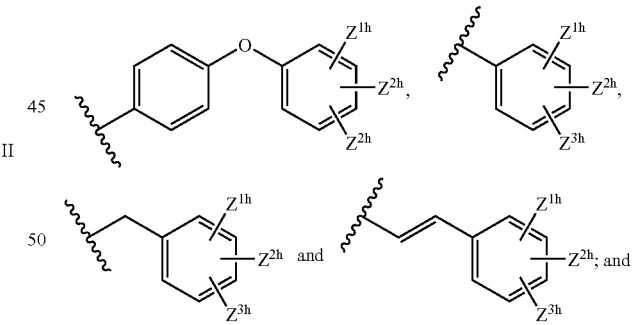

$Z^{1h-2h}$ are selected from halogen, nitro, cyano, $C_{1-6}$alkyl, $C_{1-6}$haloalkyl, and/or $C_{1-6}$alkoxy.

3. A compound of claim 2, or an enantiomer, diastereomer, salt, thereof, wherein $R^7$ is selected from:

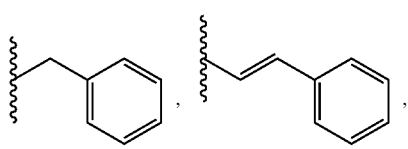

-continued

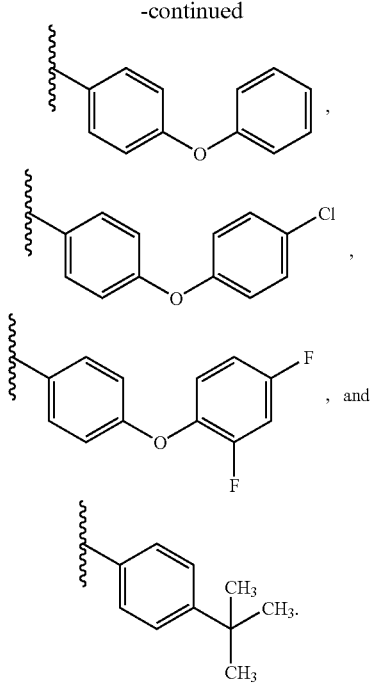

4. A compound having the formula II

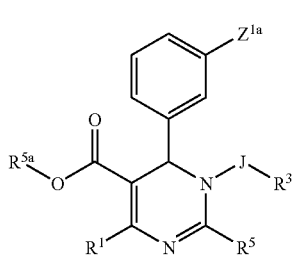

or an enantiomer, diastereomer, or salt, thereof, wherein:
$Z^{1a}$ is halo, nitro, cyano, $C_{1-6}$alkyl, $C_{1-6}$haloalkyl, or $C_{1-6}$alkoxy;
J is n-propylene;
$R^1$ is $C_{1-6}$alkyl;
$R^3$ —$N(R^6)C(O)OR^7$;
$R^{5a}$ is $C_{1-6}$alkyl;
$R^5$ is
 (c) hydrogen, $C_{1-6}$alkyl, $C_{1-6}$haloalkyl, or $C_{1-6}$alkoxy; or
 (d) phenyl optionally substituted by one or more groups selected from halo, cyano, nitro, $C_{1-6}$alkyl, $C_{1-6}$haloalkyl and/or $C_{1-6}$alkoxy; and
$R^6$ and $R^7$ are independently hydrogen $C_{1-6}$alkyl.

5. A compound selected from
(i)
  6-(3-Chlorophenyl)-1,6-dihydro-2,4-dimethyl-1-[3-[methyl(4-phenoxybenzoyl)amino]propyl]-5-pyrimidinecarboxylic acid, 1-methylethyl ester;
  6-(3-Chlorophenyl)-1,6-dihydro-2,4-dimethyl-1-[3-[methyl(phenylacetyl)amino]propyl]-5-pyrimidinecarboxylic acid, 1-methylethyl ester;
  6-(3-Chlorophenyl)-1,6-dihydro-2,4-dimethyl-1-[3-[methyl[(2E)-1-oxo-3-phenyl-2-propenyl]amino]propyl]-5-pyrimidinecarboxylic acid, 1-methylethyl ester;
  6-(3-Chlorophenyl)-1,6-dihydro-2,4-dimethyl-1-[3-[methyl(4-phenoxybenzoyl)amino]propyl]-5-pyrimidinecarboxylic acid, 1-methylethyl ester;
  1-[3-[[4-(4-Chlorophenoxy)benzoyl]methylamino]propyl]-6-(3-Chlorophenyl)-1,6-dihydro-2,4-dimethyl-5-pyrimidinecarboxylic acid, 1-methylethyl ester;
  6-(3-Chlorophenyl)-1,6-dihydro-4-methyl-2-(1-methylethyl)-1-[3-[methyl(4-phenoxybenzoyl)amino]propyl]-5-pyrimidinecarboxylic acid, 1-methylethyl ester;
  6-(3-Chlorophenyl)-1,6-dihydro-4-methyl-1-[3-[methyl(phenylacetyl)amino]propyl]-2-phenyl-5-pyrimidinecarboxylic acid, 1-methylethyl ester;
  6-(3-Chlorophenyl)-1,6-dihydro-2,4-dimethyl-1-[3-[methyl[(2E)-1-oxo-3-phenyl-2-propenyl]amino]propyl]-5-pyrimidinecarboxylic acid, 1-methylethyl ester;
  6-(3-Chlorophenyl)-1-[3-[[4-(2,4-difluorophenoxy)benzoyl]methylamino]propyl]-1,6-dihydro-2,4-dimethyl-5-pyrimidinecarboxylic acid, 1-methylethyl ester;
  6-(3-Chlorophenyl)-1-[3-[[4-(1,1-dimethylethyl)benzoyl]methylamino]propyl]-1,6-dihydro-2,4-dimethyl-5-pyrimidinecarboxylic acid, 1-methylethyl ester;
  6-(3-Chlorophenyl)-1-[3-[[4-(1,1-dimethylethyl)benzoyl]methylamino]propyl]-1,6-dihydro-4-methyl-2-(trifluoromethyl)-5-pyrimidinecarboxylic acid, 1-methylethyl ester; and
  6-(3-Chlorophenyl)-1,6-dihydro-4-methyl-1-[3-[methyl(4-phenoxybenzoyl)amino]propyl]-2-(trifluoromethyl)-5-pyrimidinecarboxylic acid, 1-methylethyl ester; or
(ii) an enantiomer, diastereomer, or salt of (i), thereof.

6. A compound of claim 5 selected from
(i)
  6-(3-Chlorophenyl)-1,6-dihydro-2,4-dimethyl-1-[3-[methyl(4-phenoxybenzoyl)amino]propyl]-5-pyrimidinecarboxylic acid, 1-methylethyl ester; and
  6-(3-Chlorophenyl)-1-[3-[[4-(1,1-dimethylethyl)benzoyl]methylamino]propyl]-1 ,6-dihydro-2,4-dimethyl-5-pyrimidinecarboxylic acid, 1-methylethyl ester; or
(ii) an enantiomer, diastereomer, or salt of (i), thereof.

7. A pharmaceutical composition comprising at least one compound of claims 1, 2, 4 or 5 and a pharmaceutically acceptable vehicle, carrier or diluent.

8. A method of treating a mammalian host to relieve hypertension comprising administering to said host in need of such treatment at least one compound of claims 1, 2, 4 or 5 and a pharmaceutically acceptable carrier or diluent.

* * * * *